United States Patent [19]

Daly et al.

[11] 4,145,082

[45] Mar. 20, 1979

[54] CRADLE FOR CONTROLLING ABNORMAL SITTING POSTURES

[75] Inventors: David M. Daly, 4116 Emerson #4, Dallas, Tex. 75202; Cynthia L. Stone, Dallas, Tex.

[73] Assignee: David M. Daly, Dallas, Tex.

[21] Appl. No.: 786,498

[22] Filed: Apr. 11, 1977

[51] Int. Cl.² .................... A47C 3/00; A47C 25/00; A61F 13/00

[52] U.S. Cl. .................................. 297/384; 128/134; 297/DIG. 4

[58] Field of Search .............. 128/70, 80 R, 133, 134; 5/327; 297/427, 384, 390, DIG. 4

[56] References Cited

U.S. PATENT DOCUMENTS

| | | | |
|---|---|---|---|
| 1,486,813 | 3/1924 | Tallman | 297/390 X |
| 2,784,775 | 3/1957 | Madsen | 297/390 |
| 3,037,813 | 6/1962 | Lowe | 297/390 |
| 3,423,773 | 1/1969 | Yamate | 297/390 X |
| 3,606,885 | 9/1971 | Lund | 128/134 |
| 3,761,126 | 9/1973 | Mulholland | 297/DIG. 4 |
| 3,863,984 | 2/1975 | Sickels | 297/427 |

Primary Examiner—James T. McCall
Attorney, Agent, or Firm—Nickolas E. Westman

[57] ABSTRACT

A support cradle for supporting a person seated in a chair by cradling the upper legs of the person, and maintaining the legs in a desired passive restraint arranged so that if the person moves the hips or legs in an abnormal degree such as excessive hip flexion, hip adduction, hip internal rotation, hip extension, scissoring or the like, the cradle will restrain such movement. The cradle provides no restraint so long as normal sitting posture is maintained. The cradle is especially useful in treatment and management of patients with neurogenic movement disorders which manifest with spasticity and abnormal movement patterns such as with spinal cord injury or in cerebral palsy.

10 Claims, 6 Drawing Figures

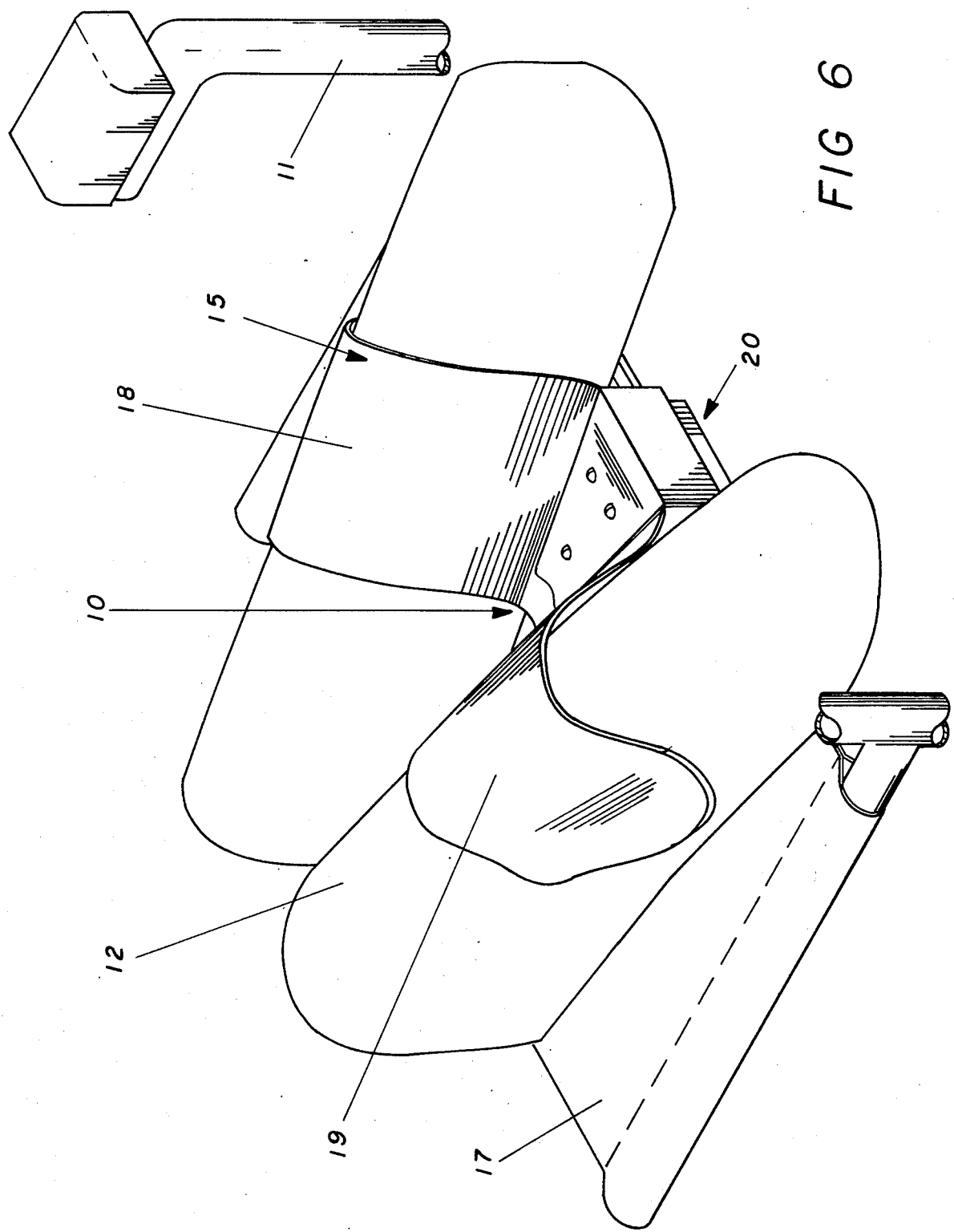

4,145,082

CRADLE FOR CONTROLLING ABNORMAL SITTING POSTURES

BACKGROUND OF THE INVENTION

1. Field of the Invention

The present invention relates to a cradling system for restraint of seated persons.

2. Prior Art

In the prior art, various restraint devices have been advanced for restraining and treating persons with spastic paralysis, such as victims of cerebral palsy. U.S. Pat. No. 3,761,126 shows an adjustable chair which is designed to restrain a patient in a large number of different locations on the person, and includes an adduction post that is connected to a cross bar on the chair and prevents the legs of the patient from scissoring or crossing. Various center post devices have also been utilized in various chairs for maintaining the legs of a person in a separated condition, which tends to aid in maintaining the seating posture reasonably normal. An example of a wheel chair that has such a post, and which also serves to prevent a person from sliding out of the chair is shown in U.S. Pat. No. 3,216,738, and another type of restraining device that keeps the feet separated is shown in U.S. Pat. No. 3,839,755, which is a mobile bed having a board for separating the feet.

Various casts also have been advanced which maintain the position of the person in the desired position, for example U.S. Pat. No. 3,563,601 shows an orthopedic cast that separates the legs substantially.

Other examples of the prior art include U.S. Pat. Nos. 2,858,882, 3,563,601; 3,572,830 and 3,635,526. An additional U.S. Pat. No. 3,381,973 shows a chair convertible to a bed which uses a knee board for keeping the knees separated when a person is using the bed.

SUMMARY OF THE INVENTION

The present invention relates to a support cradle for cradling the legs of a person with disorders, such as cerebral palsy, in which motor function is impaired by disharmony of muscle movements. Spinal cord damage also can cause such impairment of motor functions.

Simplified definition of terms used in this specification may be helpful. Hip flexion is a movement wherein the knees tend to move upwardly; hip adduction is, briefly, a lateral or sideways movement of the hips while seated; hip extension is movement of the hips forwardly (and perhaps upwardly) while seated. An example of hip internal rotation is rotation of the right leg and hip when turning the right foot counterclockwise and is included in the movements which the cradle restrains. Scissoring can be described as a combination of hip adduction, hip internal rotation, and hip extension and manifests itself by a tendency of the legs to cross.

The term appropriate sitting posture is used in certain contexts to indicate postures in which asymmetries of positioning are required for example, when the extent of impaired motor functioning is not symmetric. Such postures, while they may not be considered strictly normal postures are desired postures or positions.

The cradle of the present invention guides or controls the position of the person's legs and hips to tend to separate the legs, and forms a passive restraint when the patient is sitting in a normal or an appropriate posture. If the patient moves abnormally, such as by adducting the hip excessively, the restraint will resist small movements, and with larger attempted movements greater restraint will be exerted to discourage such abnormal movement. A tendency of the legs to move together or to scissor is also restrained by the present device, and in addition excessive hip flexion, excessive hip internal rotation, and excessive hip extension are resisted at different locations on the support or cradle.

The support means onto the seat of a chair or other seat which is being used by the person, and cradles the legs from adjacent to the hip to adjacent to the knee, that is, along substantial length of the upper leg and thigh as opposed to a narrow band support or restraint.

The forward surfaces of the restraint will tend to restrain the legs and prevent excessive hip flexion, that is when the knees tend to move upwardly, and excessive hip extension would be resisted at the rear portions of the restraint. The area of the restraint is sufficiently large to prevent localized pressures on the legs or thighs from being excessive and causing discomfort. Likewise, the length of the support provides a gentle initial restraint when there is excessive hip adduction or excessive hip internal rotation, or when scissoring of the legs is encountered.

The cradle is made of a slightly flexible (fiberglass) material so there is some slight amount of give to the material and this also tends to resiliently increase the resistance of movement as greater forces are applied without completely blocking movement in its entirety. A plastic material sold under the trademark "Orthoplast" is highly suitable in that it can be formed and reformed quickly to custom fit the cradle.

The cradle is easy to manufacture and may be formed to suit a particular patient or made in general sizes for a large number of patients. The restraint is made so that at appropriate positions there is generally a space between the legs being cradled and the cradle itself, but any excessive, abnormal movements are positively restrained.

The cradle can be attached to chairs, or can be made with a fixedly attached seat board. The positive positioning of the patient in a normal seated position minimizes problems with the hip joints from excessive pressures at abnormal locations, which occur when the hips are abnormally moved. Further, the device tends to train the person to maintain appropriate positions when seated, which is the position that a large number of such persons must maintain through most of their waking hours.

BRIEF DESCRIPTION OF THE DRAWINGS

FIG. 6 is a perspective view of the cradle showing it in use.

DESCRIPTION OF THE PREFERRED EMBODIMENTS

The cradle of the present invention is shown generally at 10, and as can be seen, it can be used in combination with a wheel chair 11, or any other type of seat support for a cerebral palsy patient represented in out-line at 12. The cradle 10 is made to restrain abnormal movements of the legs, hips and associated portions of the patient 12. On the other hand, the cradle is made so that it will not substantially restrain normal movements, and will encourage a person to sit in a normal manner.

When persons with a spinal cord injury or cerebral palsy are seated, they are particularly vulnerable to excessive hip flexion, hip adduction, hip internal rotation, hip extension, to extensor thrusting and to scissoring. These cause uneven weight bearing on portions of the anatomy, and can cause serious inflamations, and problems with the hip joints. Unnatural sitting positions can be reduced or eliminated through the proper modulation and control of flexion, extension, rotation and adduction.

Figure 1:
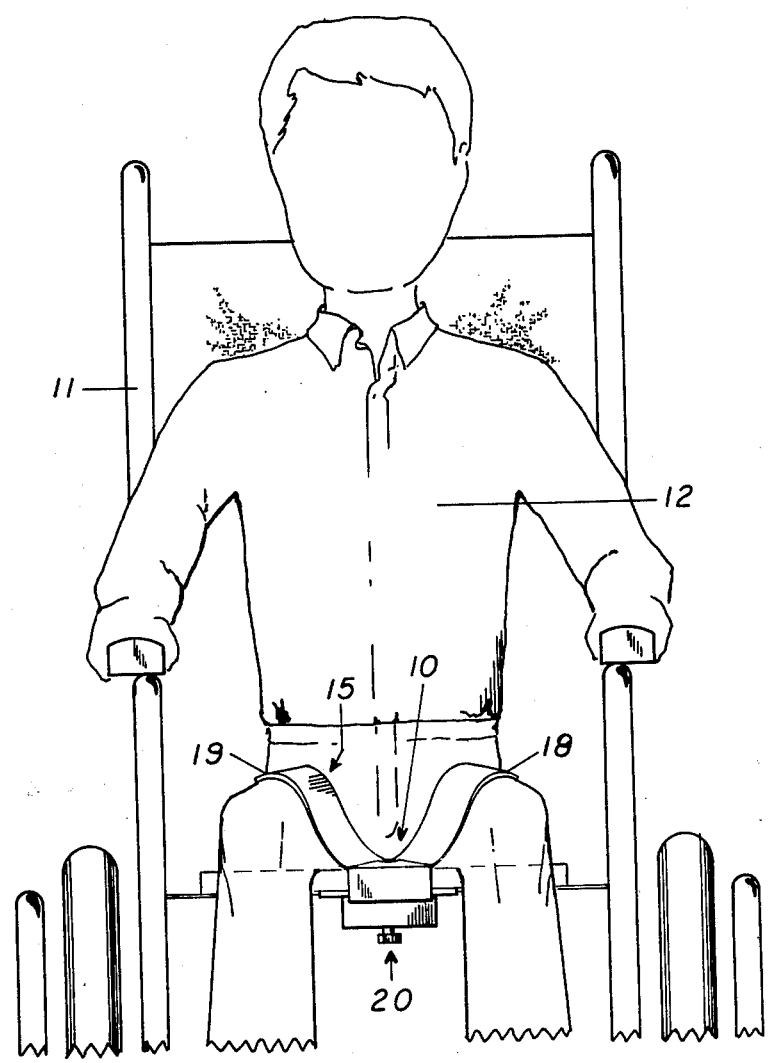
FIG. 1 is a fragmentary front elevational view of a typical wheel chair having a cradle made according to the present invention installed thereon.
Figure 2:
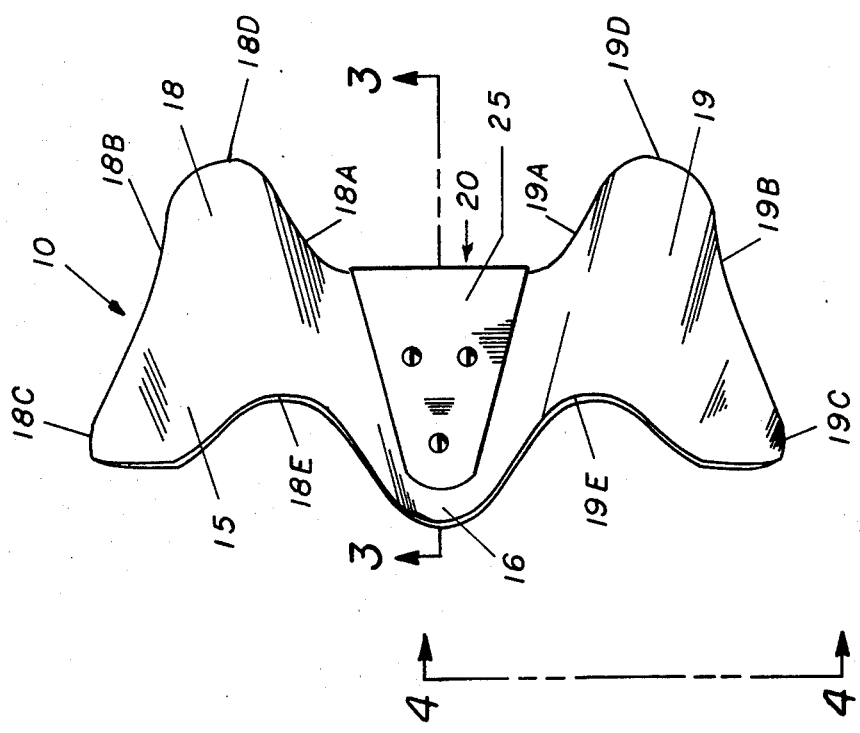
FIG. 2 is a top plan view of the cradle of FIG. 1.
Figure 3:
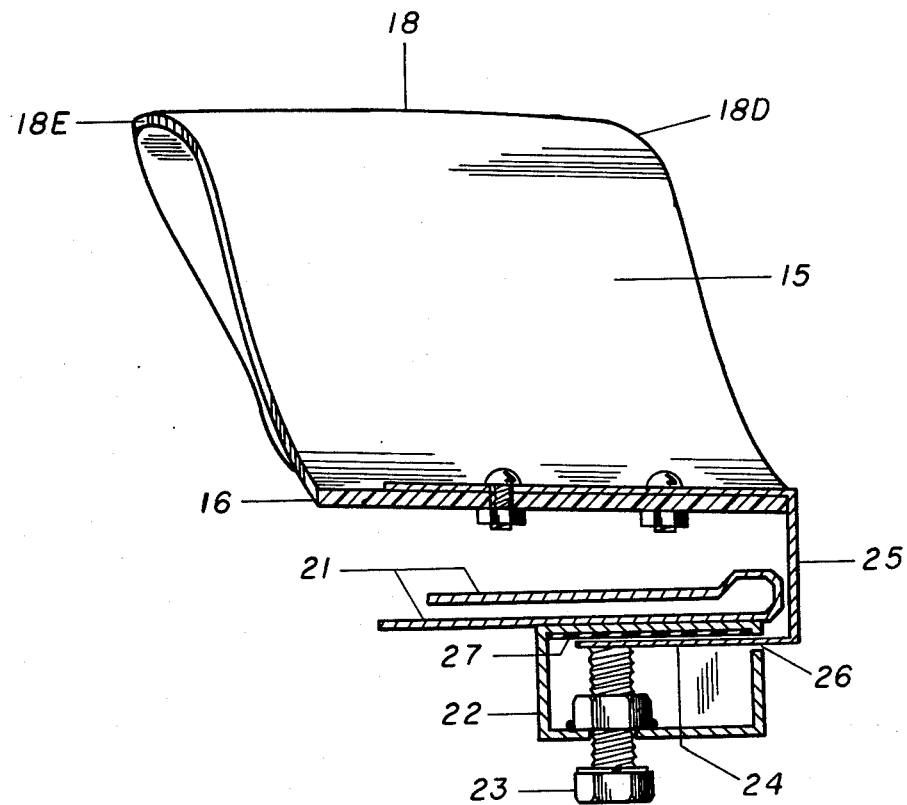
FIG. 3 is a sectional view taken as on line 3—3 in FIG. 2.
Figure 4:
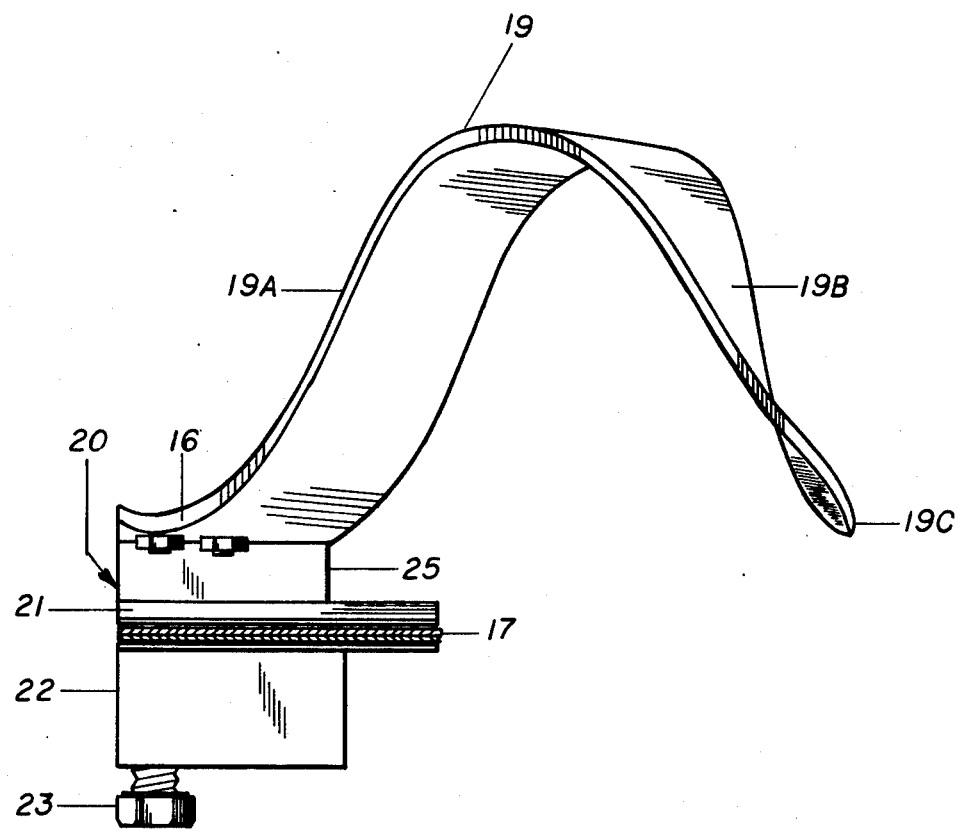
FIG. 4 is a sectional view taken as on line 4—4 in FIG. 2.

The cradle 10 as perhaps best seen in FIGS. 2, 3, 4 and 5, comprises a unitary, molded piece of flexible, or semirigid fiberglass reinforced plastic 15. The cradle is generally symmetrically molded, and has a center mounting portion illustrated generally at 16 which rests adjacent to the seat 17 on which the cradle is to be supported. In the present invention, the center portion 16 is spaced slightly from the seat itself through the particular clip or clamp arrangement being utilized for securing the cradle in place. A pair of inverted upper leg receiving receptacles 18 and 19 are formed on opposite sides thereof, which extend in fore and aft direction and are positioned so that they diverge from a common center that would represent the intersection of central axes of the upper legs of a person seated symmetrically on the seat 17. The receptacles 18 and 19 are formed by inverted, generally U shaped portions. The U shaped portions are made so that they taper and have less clearance from the seat adjacent the forward (or lower) portions of the upper leg, or in other words closer to the knee, and have inner walls 19A and 18A that start at center portion 16 and taper upwardly, and walls 18B and 19B that taper downwardly toward the seat 17, and clear the seat with only a small amount of space. Rounded end tabs 18C and 19C, respectively, can also be provided to remove any sharp edges that might tend to cut or snag the patient or his clothing. The forward ends of the receptacles 18 and 19, as indicated at 18D and 19D, respectively, are also rounded to minimize any tendency to create a pressure point if the leg is moved against the forward ends. Likewise, the base or rear ends which are the ends of receptacles 18 and 19 closest to the hip are curved forwardly slightly as indicated at 18E and 19E, respectively. The center portions of the walls forming receptacles 19 and 19 are spaced above the top surface of the seat 17 as shown in FIGS. 3 and 4, perhaps best, and are spaced a sufficient distance so that the legs of a patient using the cradle fit underneath without tightness or discomfort. There can be some loose fitting, particularly between the upper surface of the leg and the upper portions of the inverted receptacles 18 and 19, to permit some normal movement of the legs without any substantial restraint. When a patient is seated and centered on the seat 17, the legs in the cradle will diverge from the hips outwardly in a normal fashion, and therefore tend to encourage the person to remain seated in a symmetrical position with no abnormal pressure points on the body while seated. A cushion is normally used on the seat.

It can be seen that the center portion 16 is secured to the seat with a clamping arrangement indicated generally at 20, so that the cradle is held onto the forward portions of the seat 17 and in the center of the seat. The clamping member 20, which can be any desired configuration, will be more fully explained later, but once the patient 12 is in position on seat 17 the cradle is placed over the legs and clamped to the seat. The patient's legs pass through the receptacles 18 and 19 and if the patient moves so that there is excessive hip adduction, often called a "windswept" position, in other words, if the hips are slid over into a corner of the chair to the left for example, which would be upwardly in relation to FIG. 2, the right leg would also tend to move to the left, and the wall portion 19A on the inside of the inverted receptacle 19 would start to resist this movement. Any small movement would start the leg to engage the wall 19A and tend to resist the adduction to the left. Larger movements would cause the left leg to start to engage wall portion 18B, and then both walls 19A and 19B would be resisting adduction to the left. The greater the movement, the greater the resistance. This resistance tends to urge the patient to relocate toward the center of the seat. When the patient is in normal position there is no active restraint.

Hip adduction to the right, which would be downwardly in FIG. 2, would cause opposite restraint, that is the left leg would tend to first be resisted by the wall portion 18A and with greater hip adduction to the right, the panel 19B would tend to restrain the right leg as well. Because the plastic member 15 is somewhat resilient, it will tend to return the person to the centered position.

It should be noted that the inverted receptacles 18 and 19 are generally fairly long in relation to the length of the upper leg of the patient. In other words, the upper wall portions of receptacles 18 and 19 should cover or span a length of the upper leg sufficient to provide a large surface area for restraining abnormal movements and not causing any "digging in" of edges or narrow bands.

In the case of excessive hip flexion, which is a movement where the knees tend to move upwardly toward the chest, it can be seen that the forward edges 18D and 19D will immediately resist any excessive movement upwardly, causing the patient to return to a normal sitting position with the legs generally flat on the seat, and bearing a portion of the patients weight to prevent abnormal seated positions.

Excessive hip extension, which is a tendency of the hips to move forwardly (and perhaps upwardly), or the knees to move downwardly, depending on how it is viewed, will be resisted at the rear portions of the cradle adjacent to edges 18E and 19E. Again, the resistance to movement will be across a relatively large area and because there is only a slight amount of clearance between the receptacles 18 and 19 and the leg, this resistance will occur almost immediately.

The cradle is therefore a modulating device that permits some movement toward an abnormal position, but immediately starts to restrain, and does restrain at increasingly greater resistances as more movement is attempted.

Figure 5:
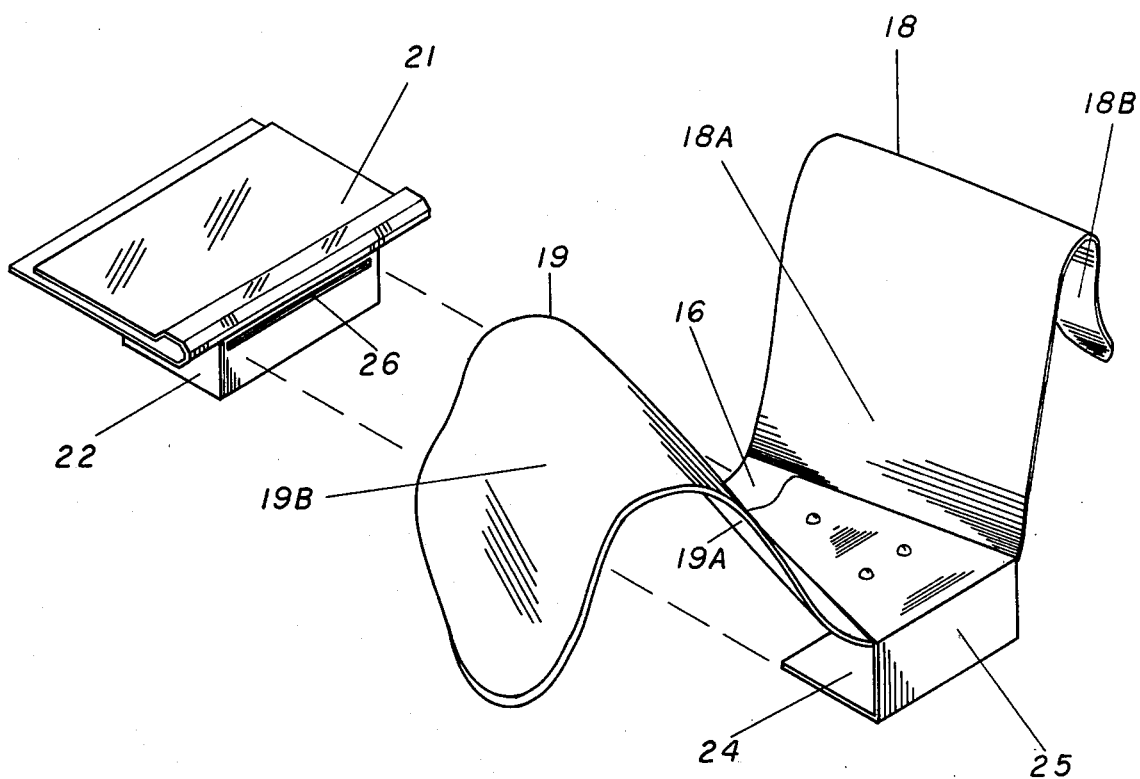
FIG. 5 is an exploded perspective view of the cradle of FIG. 2.

The means for attaching the cradle to a seat support can be widely varied and range from having a screw or bolt that fastens the center portion 16 to the top of the seat after the patient is seated, to the use of an ordinary "C" clamp. However, one type of such clamp 20 that permits the cradle to be easily removed and replaced is shown in FIGS. 3 and 5. A separate mounting clip indicated generally at 21 is of size to pass over the seat 17, and if spring loaded will remain in position relatively easily. It can be fixed in place if desired. The clip 21 carries a box cross section member 22 on the bottom surface thereof. The member 22 has a screw 23 threaded through a nut that is fixed to the lower wall. The screw 23 can be a thumb screw if desired. A second clip 25 is fixedly attached to the center portion 16 of the cradle and second clip 25 has a lower leg 24 that fits through a provided slot 26 in the forward wall of the member 22. The lower leg 24 of the clip 25 can then be clamped upwardly against a resilient or high friction layer (for providing friction holding force) indicated at 27 by tightening the screw 23 against the leg 24. The layer 27 is thus compressed and the clip 25 is secured to hold the cradle in position. The screw 23 can be released easily, and the leg 24 withdrawn from the member 22 for removing the cradle to permit the patient to be removed from the chair, and the cradle may be easily replaced when the patient is again seated.

The cradle 10 can be molded from any suitable plastic material, and may use fiberglass reinforced plastic if desired. The cradle may be made in a variety of sizes to provide standard sizes for a number of different patients, or can be easily molded or formed for individual use if desired. The cost is low either way. The walls forming the inverted receptacles 18 and 19 are attached only at the center which provides some "wing like" deflections, but the walls do provide increasing resistance to increasing abnormal movements. The device provides substantially no restraint when the patient is normally seated, that is symmetrically located with respect to the bisecting center line of the cradle.

The cradle is not restricted to use with wheel chairs, but can be used with any type of seat support for a patient. Of course it is also apparent that scissoring, or a tendency of the legs to cross or the knees to move together is restrained by both of the inverted members 18 and 19, along the wall portions 18A and 19A, respectively.

What is claimed is:

1. A support cradle for providing restraint of the upper legs and hips of a seated person comprising a pair of wall members, means to attach said wall members to a seat on which a seated person is to be positioned, said wall members each forming an inverted downwardly open receptacle having first wall portions overlying the upper legs of a person seated in a desired position and having integral second wall portions to form side walls to restrain lateral movement of legs within said receptacles from a desired position, said downwardly open receptacles having longitudinal axes extending generally parallel to a seat on which the support cradle is mounted, said longitudinal axes diverging in direction outwardly from the rear of a seat on which the cradle is supported, said receptacles being formed from material which resiliently increases the resistance of movement of a person whose legs are within said receptacles and is thereby restrained, to permit limited movement of a person restrained and substantially immediately start to restrain undesirable movement comprising hip flexion, hip adduction, hip internal rotation and hip extension, said second wall portion on the outer sides of said receptacles being free to move resiliently upwardly from the seat and the first wall portions restraining substantial upward movement of the legs of a person restrained.

2. The support cradle of claim 1 wherein said wall members are attached to a common wall portion between said wall members, said common wall portion forming the sole location of said means to attach.

3. For use in combination with a seat for supporting a person, which seat has a support surface on which a person may sit with the upper legs from the hips to the knees generally horizontal, said seat having a rear portion adjacent the hips and a front edge portion adjacent the knees of a person supported on the seat, and having a fore and aft extending central axis, a support cradle for restraining the legs of a person seated on said seat including a pair of wall members each comprising an upwardly sloping first wall portion adjacent said central axis, an upper wall portion joining said first wall portion and a second wall portion sloping downwardly from and joined to said upper wall portion, said wall portions of each wall member being of size to fit over and be closely spaced from a leg of a person seated on said seat, said wall members diverging in direction from the rear portions of the seat toward the forward portions of the seat, whereby the legs of a person seated are spaced in a desired diverging position and means to mount said wall members to said seat, said wall members being molded to a common member between the pair of wall members and being molded from a material which resiliently increases resistance to mount as greater forces are applied and to generally conform to the contour of a seated persons legs to provide side restraint on legs of a seated person at the rear of the wall members, and to provide substantial upward restraint of a seated persons legs at the front of the wall members.

4. The combination of claim 3 wherein said wall members comprise a unitary wall assembly contoured to restrain excessive hip flexion, hip adduction, hip internal rotation, and hip extension of a person seated on the seat with his legs within the receptacles formed by said wall members, and said means to mount is connected only to the common member, the outer edges of said wall member being otherwise unattached to said seat.

5. The combination of claim 3 wherein said means to mount comprises a releasable clip attached to said common member and fastened adjacent the central axis, said means to attach being the only connection between said seat and wall members and being connected only to said common member.

6. A support cradle for providing restraint of the upper legs and hips of a seated person comprising first and second wall members, a common wall between and connected to said pair of wall members to support said wall members, each of said first and second wall members forming an inverted downwardly open receptacle positioned to closely overlie one leg of a person seated in a desired position and said wall members each including two wall portions to form side walls to restrain lateral movement of a leg within said receptacles from a desired position, and means to attach said support cradle to a seat only through said common wall.

7. A method of restraining and supporting persons with neurogenic movement disorders which manifest with spasticity and abnormal movement patterns such as with spinal cord injury and in cerebral palsy while seated on a generally horizontal seat comprising the steps of placing substantial portions of the upper legs of the person under elongated walls with the legs in a position generally diverging from the person's body toward the knee without immobilizing pressure points along the upper leg when the person is in a normal seated posture, and shaping the elongated walls from material which resiliently increases resistance to movement as greater forces are applied to the elongated walls to permit limited normal movement of the hip joints, and to restrain and prevent excessive hip flexion, hip adduction and hip internal rotation of a seated person with increasingly greater restraint from a symmetrical seated posture.

8. The support cradle of claim 6 wherein said means to attach includes a clip member releasable secured to a seat on which the cradle is to be mounted.

9. The support cradle of claim 6 wherein said wall members are made of a fiberglass reinforced plastic material.

10. The support cradle of claim 6 wherein said wall members and common wall portion are integrally formed as a unitary member.

* * * * *